United States Patent [19]

Nazerian et al.

[11] 4,388,298

[45] Jun. 14, 1983

[54] PROPAGATION OF HEMORRHAGIC ENTERITIS VIRUS IN A TURKEY CELL LINE AND VACCINE PRODUCED

[75] Inventors: Keyvan Nazerian, East Lansing; Aly M. Fadly, Holt, both of Mich.

[73] Assignee: The United States of America as represented by the Secretary of Agriculture, Washington, D.C.

[21] Appl. No.: 398,001

[22] Filed: Jul. 14, 1982

[51] Int. Cl.$^3$ .......................... A61K 39/12; C12N 7/08
[52] U.S. Cl. ...................................... 424/89; 435/235; 435/236; 435/237
[58] Field of Search .................. 424/89; 435/235, 236, 435/237

[56] References Cited

PUBLICATIONS

Domermuth et al., "Hemorrhagic Enteritis", in Diseases of Poultry, 7th Ed., M. S. Hofstad et al., eds., pp. 590–595 (1978).
Fasina et al., Avian Diseases 26(1): 150–157 (1982).
Nazerian et al., Int. J. Cancer 29: 63–68 (1982).

*Primary Examiner*—Sam Rosen
*Attorney, Agent, or Firm*—M. Howard Silverstein; David G. McConnell; Curtis P. Ribando

[57] ABSTRACT

A lymphoblastoid cell line of turkey origin designated as MDTC-RP-19 and deposited under the ATCC Accession No. CRL-8135 has been found useful for the in vitro propagation of hemorrhagic enteritis virus (HEV). Cocultivation of the apathogenic strain of HEV with the cell line is useful in the production of a vaccine for protecting fowl against virulent HEV.

6 Claims, No Drawings

PROPAGATION OF HEMORRHAGIC ENTERITIS VIRUS IN A TURKEY CELL LINE AND VACCINE PRODUCED

BACKGROUND OF THE INVENTION

1. Field of the Invention

Hemorrhagic enteritis (HE) is an economically important disease of turkeys characterized by hemorrhaging in the gut, enlargement of the spleen, depression, and often sudden death. It accounts for annual losses in the turkey industry amounting to millions of dollars. The disease is caused by a type II avian adenovirus, hemorrhagic enteritis virus (HEV), which also causes a syndrome in chickens and pheasants known as marble spleen disease. HEV is serologically distinct from all other known avian adenoviruses, and is unique among adenoviruses in its inability to grow in ordinary cell cultures. Accordingly, bird inoculation has been the only available assay for its detection and no in vitro method for vaccine production has previously existed.

This inventon relates to a successful procedure for the in vitro propagation of HEV and to the application of this procedure to the production of an HE vaccine and as a bioassay technique for determining the vaccine potency.

2. Description of the Prior Art

As reported by Domermuth et al. [Hemorrhagic enteritis. In: Diseases of Poultry, 7th ed. (M. S. Hofstad, B. W. Calnek, C. F. Helmbolt, W. M. Reid, and H. W. Yoder, eds.) pages 590–595. Iowa State University Press, Ames, Iowa (1978)], previous attempts to propagate HEV strains in conventional embryo and fibroblast cell cultures have been unsuccessful. Facina et al. [Avian Disease 26: 150–157 (1982) ] demonstrated the possible infection of chicken, turkey, and pheasant spleen cells with HEV, but all attempts to passage the virus in these cultures failed. Absent a method for the continued in vitro propagation of the vaccine virus, spleen homogenates from infected birds have been the only agents available for inducing immunity. The inherent impurity of cell-associated viruses has precluded the Federal licensing of such homogenates for commercial use as vaccines. Moreover, they do not lend themselves to lyophilization, and therefore require special facilities for storage. As an alternative to vaccinal inoculation, Domermuth et al., supra, also teaches that poults can be passively immunized by direct injection of convalescent antiserum from recovered flocks. Of course, widespread application of such an approach would be precluded by the unfeasibility of collecting ample antiserum coupled with uncertainty as to its nonpathogenicity.

SUMMARY OF THE INVENTION

We have now surprisingly discovered that HEV can be cultivated in vitro by inoculating a lymphoblastoid cell line of turkey origin having the characteristics of MDTC-RP-19, Nazerian et al. [Int J. Cancer 29: 63–68 (1982)]. This method is useful in the propagation of both virulent and avirulent strains of HEV and in the preparation of cell-free vaccines effective against HE.

In accordance with this discovery, it is an object of the invention to achieve the unprecedented, sustained replication in cell culture of both virulent and apathogenic isolates of HEV.

It is also an object of the invention to provide a commercially acceptable process for producing a pure, cell-free vaccine for immunizing turkeys and other avian species against HEV.

Another object of the invention is to establish a bioassay system for determining the potency of the cultivated vaccine virus.

Other objects and advantages of the invention will become readily apparent from the ensuing description.

DETAILED DESCRIPTION OF THE INVENTION

The lymphoblastoid cell line, MDTC-RP-19 (RP-19) has been deposited in the American Type Culture Collection in Rockville, MD, and assigned Accession No. ATCC CRL-8135. Its origin and known characteristics have been previously described in Nazerian et al., supra, herein incorporated by reference. The deposited line represents the 13th passage from the original liver tumor suspension. For purposes of cultivating HEV in accordance with the invention, either this cell line or any cell line having the characteristics of RP-19, including subcultures thereof, would be useful. The cell line culture is free from several known tumorgenic avian viruses including avian leukosis virus, avian reticuloendotheliosis virus, and turkey lymphoproliferative disease virus, as well as the herpesvirus of turkeys. Although the line is latently infected with Marek's disease virus, its growth medium is completely noninfectious. The supernatant fluid of HEV-infected cultures therefore does not contain any other unrelated virus and can be used as a good source of pure HEV.

The cells are cultured as a suspension by plating in a nutrient medium at a concentration of about $5 \times 10^6$ cells/ml. An exemplary nutrient suitable for this purpose is a 1.8:1.0 mixture of Leibovitz L-15 medium and McCoy's modified medium (Table I, below) supplemented with 20% chicken serum, 10% bovine fetal serum, and 5% tryptose phosphate broth. Of course it is understood that other formulations could be substituted provided that they support cell propagation. Under the preferred conditions of 41° C. in 5% $CO_2$ humid atmosphere, the cells multiply 10-fold in approximately 48 hours, thereby requiring passage to fresh medium. We have found that susceptibility of RP-19 cell line to infection with HEV begins to decline on about the 35th serial passage, and is almost nil after about the 100th passage. It is therefore preferred to employ cultures passaged less than about 35 times, and more preferably not over about 25 times. However, once the cells are infected, cytopathology not only persists but also is further increased with culture passage.

TABLE 1

| Component | mg./l. |
|---|---|
| McCoy's 5a Medium (Modified)[1,2,3] | |
| Inorganic salts: | |
| $CaCl_2$ (anhyd.) | 100.00 |
| KCl | 400.00 |
| $MgSO_4$ (anhyd.) | 97.67 |
| NaCl | 6460.00 |
| $NaH_2PO_4 \cdot H_2O$ | 580.00 |
| Other components: | |
| Bacto-peptone | 600.00 |
| D-Glucose | 3000.00 |
| Glutathione (reduced) | 0.50 |
| Phenol red | 10.00 |
| Amino acids: | |
| L-Alanine | 13.90 |
| L-Arginine HCl | 42.10 |
| L-Asparagine | 45.00 |
| L-Aspartic acid | 19.97 |

TABLE 1-continued

| Component | mg./l. |
|---|---|
| L-Cysteine | 31.50 |
| L-Glutamic acid | 22.10 |
| L-Glutamine | 219.20 |
| Glycine | 7.50 |
| L-Histidine HCl.H$_2$O | 20.96 |
| L-Hydroxyproline | 19.70 |
| L-Isoleucine | 39.36 |
| L-Leucine | 39.36 |
| L-Lysine HCl | 36.50 |
| L-Methionine | 14.90 |
| L-Phenylalanine | 16.50 |
| L-Proline | 17.30 |
| L-Serine | 26.30 |
| L-Threonine | 17.90 |
| L-Tryptophan | 3.10 |
| L-Tyrosine (disodium salt) | 26.20 |
| L-Valine | 17.60 |
| Vitamins | |
| Ascorbic acid | 0.50 |
| Biotin | 0.20 |
| Choline chloride | 5.00 |
| D-Ca pantothenate | 0.20 |
| Folic acid | 10.00 |
| i-Inositol | 36.00 |
| Nicotinamide | 0.50 |
| Nicotinic acid | 0.50 |
| Para-aminobenzoic acid | 1.00 |
| Pyridoxal HCl | 0.50 |
| Pyridoxine HCl | 0.50 |
| Riboflavin | 0.20 |
| Thiamine HCl | 0.20 |
| Vitamin B$_{12}$ | 2.00 |

[1]McCoy, T. A., Maxwell, M., and Kruse, P. F., Proc. Soc. Exper. Biol. & Med., 100: 115-118 (1959).
[2]Hsu, T. C., and Kellogg, D. S., Jr., Nat'l. Cancer Inst., 25: 221 (1960).
[3]Iwakata, S., Grace, J. T., Jr., N.Y. J. Med., 64(18): 2279-2282 (Sept. 15, 1964).

L-15 (Leibovitz) Medium[1]

| Inorganic salts: | |
|---|---|
| CaCl$_2$ (anhyd.) | 140.00 |
| KCl | 400.00 |
| KH$_2$PO$_4$ | 60.00 |
| MgCl$_2$ (anhyd.) | 93.68 |
| MgSO$_4$ (anhyd.) | 97.67 |
| NaCl | 8000.00 |
| Na$_2$HPO$_4$ (anhyd.) | 190.23 |
| Other components: | |
| D(+) Galactose | 900.00 |
| Phenol red | 10.00 |
| Sodium pyruvate | 550.00 |
| Amino acids: | |
| DL-α-Alanine | 450.00 |
| L-Arginine (free base) | 500.00 |
| L-Asparagine | 250.00 |
| L-Cysteine (free base) | 120.00 |
| L-Glutamine | 300.00 |
| Glycine | 200.00 |
| L-Histidine (free base) | 120.00 |
| DL-Isoleucine | 250.00 |
| L-Leucine | 125.00 |
| L-Lysine (free base) | 75.00 |
| DL-Methionine | 150.00 |
| DL-Phenylalanine | 250.00 |
| L-Serine | 200.00 |
| DL-Threonine | 600.00 |
| L-Tryptophan | 20.00 |
| L-Tyrosine | 300.00 |
| DL-Valine | 200.00 |
| Vitamins: | |
| DL-Ca pantothenate | 1.00 |
| Choline chloride | 1.00 |
| Folic acid | 1.00 |
| i-Inositol | 2.00 |
| Nicotinamide | 1.00 |
| Pyridoxine HCl | 1.00 |
| Riboflavin-5'-phosphate, sodium | 0.10 |
| Thiamine monophosphate | 1.00 |

[1]Leibovitz, Albert, Am. J. Hyg. 78: 173-180 (1963).

The virulent (VHEV) and the avirulent vaccine (AHEV) strains of HEV can each be cocultivated with the aforementioned growing cell line. The two strains of HEV are similar in terms of morphology, the cytopathology toward the cell line, and the nature of their viral antigens; but they differ in their pathogenicity for the bird. The virulent HEV causes enlargement of spleen, hemorrhagic lesions in the gut, and death, whereas, the avirulent vaccine HEV only causes a transient enlargement of the spleen with no hemorrhagic lesions or death.

A suspension of the RP-19 cell line is inoculated either by the addition of cells infected with the appropriate HEV strain, or else by contact with cell-free supernatant fluid from previously infected cultures. The preferred cultivation conditions are the same as those described above for the uninfected cell culture except that in the nutrient medium, the chicken serum is reduced to 5%, the bovine fetal serum to 2%, and the tryptose phosphate broth to 1%.

Adenoviruses cause drastic changes in the metabolic condition of the infected cell, eventually killing it. A similar result occurs in RP-19 cultured cells after infection with VHEV or AHEV. An unusual enlargement of infected cells occurs concomitant with the development of intranuclear inclusion bodies typical of adenoviruses. These changes are paralleled with synthesis of HEV specific antigens that are demonstrated by their reaction with specific antibodies to HEV in serological tests such as immunofluorescence. Finally, these changes are followed by synthesis of complete infectious virus particles that are released into the culture medium after rupture of the cell.

The growth rate of the cell ine in a given suspension will be diminished as a function of the extent of infection. Passage onto fresh medium will maintain the viability and enhance the propagation of uninfected cells. Serial passage onto fresh cell line results in enrichment of the HEV, with the maximum titer being obtained after 4-5 passages.

In preparing a vaccine for use in inoculating turkeys against HEV, cells and other debris are separated from the infected suspension by centrifugation, filtration, or other conventional separatory method as known in the art. The recovered supernatant fluid is consistently a reliable source of pure HEV in that it is free of any other viruses. It can be formulated into a vaccine at a desired predetermined dosage by dilution with additional medium or other physiological solutions, or with a pharmaceutically acceptable carrier. An infectious endpoint titer for HEV samples can be obtained in the CRL-8135 cell line cultures based upon limiting dilution and appearance of cytopathology. In this manner, the system is operative as a bioassay for determining sample potency and the requisite dilution rate for proper dosaging.

It is envisioned that vaccinal amounts of the vaccine would be administered by conventional methods to protect against HE in turkeys and marble spleen disease in chickens and pheasants. Insofar as the avirulent HEV is known to protect fowl against virulent HEV with minimal pathogenicity, it of course would be the preferred strain for use in vaccine production.

The following examples are intended only to further illustrate the invention and are not intended to limit the scope of the invention which is defined by the claims.

EXAMPLE 1

A. Three-week-old Beltsville small white turkey poults from a pathogen-free flock were orally inoculated with 0.2 ml. of 1:10 dilution of turkey spleen homogenate containing Virginia virulent HEV. Six days later, the turkeys were killed and enlarged spleens were asceptically removed, minced, and made into suspension in nutrient medium A described in Table II, below. Single cell suspensions from spleen homogenates were mixed with $10 \times 10^6$ cells from MDTC-RP-19 cultures in nutrient medium A (Table II) and allowed to incubate at 41° C. in 5% $CO_2$ and humid atmosphere. After 48 hours, cells 5–6 times larger than uninfected cells were observed in the cultures. Additional fresh RP-19 cells were added to these infected cultures and similarly incubated at 41° C. After 5–6 similar passages in medium B, supernatant fluids from cultures with numerous enlarged cells were collected by decantation, centrifuged at 1000 r.p.m. and filtered through 450 µm. filters to remove cells and cellular debris.

TABLE II

| Component | Percent by volume | |
|---|---|---|
| | Nutrient medium A | Nutrient medium B |
| Liebovitz/McCoy (1.8:1) medium | 65 | 92 |
| chicken serum | 20 | 5 |
| bovine fetal serum | 10 | 2 |
| tryptose phosphate broth | 5 | 1 |
| | 100 | 100 |

B. Filtered fluids from Example 1A were used for infection of fresh uninoculated MDTC-RP-19 cultures in medium B. Specific morphological changes appeared in these cultures within 48 hours. Virulent HEV infected MDTC-RP-19 cultures at several passage levels were mixed in nutrient medium A with 10% DMSO and stored at −196° C. in liquid nitrogen. Cell-free virulent HEV infectious supernatant fluids from these infected cultures were collected, centrifuged at 1000 r.p.m. and stored in 4 ml. aliquots at −70° C.

EXAMPLE 2

A. The procedure of Example 1A was repeated except that Virginia avirulent vaccine HEV was substituted for the virulent isolate. B. The procedure of Example 1B was repeated using the filtered fluids from Example 2A as inoculant for fresh MDTC-RP-19 cultures in medium B. Cell-free supernatant fluids from highly infected cultures containing infectious live avirulent vaccine HEV were collected and stored in 4 ml. aliquots at −70° C.

EXAMPLE 3

The influence of passaging on the susceptibility of MDTC-RP-19 cells to infection with virulent and avirulent vaccine HEV was tested. Cells from various passages of the cell line suspended in nutrient medium A were infected with either cell-free VHEV or cell-free AHEV as in EXAMPLES 1B and 2B and were observed with the light microscope for morphological changes. Highly passaged cells (135th passage) were completely resistant to infection with either VHEV or AHEV whereas low passaged cells (11th passage) were very susceptible in that initial infection caused a rapid appearance of cytopathology that persisted and further increased with culture passage. The intermediate passaged cells (35th passage) were also susceptible but somewhat less than that of the low passaged cells. Examination of infected cells by immunofluorescence and electron microscopy revealed the presence of HEV antigens and virus particles in low and medium passaged cultures.

EXAMPLE 4

A culture of MDTC-RP-19 cells infected with cell-free pathogenic HEV as described in Example 1B was serially passaged every 48 hours. On the 10th passage, the supernatant fluid was collected and filtered. Two-tenths ml. of the undiluted fluid was used to orally infect each of six 3-week old Beltsville small white turkey poults. At 10 days post challenge, the six poults were sacrificed and examination revealed HE related lesions in all six, indicative of successful replication and passaging of the HEV in the cultured cell line. In a control group of seven uninocculated poults, none displayed HE related lesions.

EXAMPLE 5

A group of 2-week-old turkey poults were vaccinated orally with 0.2 ml. of $10^{-1}$ dilution of AHEV propagated in MDTC-RP-19. A group of hatchmate poults were kept unvaccinated. Two weeks later all turkey poults were orally inoculated with 0.2 ml. of cell culture-propagated VHEV. All turkeys in the vaccinated group were protected against HE and showed no clinical symptoms or lesions of the disease. The unvaccinated turkeys developed typical clinical symptoms and suffered a 37% mortality with HE lesions.

It is understood that the foregoing detailed description is given merely by way of illustration and that modification and variations may be made therein without departing from the spirit and scope of the invention.

We claim:

1. A method for the in vitro propagation of hemorrhagic enteritis virus (HEV) comprising:
   a. inoculating with said virus a suspension of lymphoblastoid cells in a medium suitable for growth of said cells, wherein said cells have the characteristics of the MDTC-RP-19 cell line; and
   b. culturing said inoculated cell suspension under conditions suitable for propagation of said virus.

2. A method as described in claim 1 wherein said virus is an avirulent strain of HEV.

3. A method as described in claim 1 wherein said cell line is that identified by ATCC Accession No. CRL-8135 or a subculture thereof.

4. A method as described in claim 1 further comprising repeatedly serially passaging and culturing said inoculated cell suspension until substantially all the cells in the culture are infected, and thereafter recovering the supernatant fluid from said culture.

5. A vaccine for use in the immunization of turkeys and other avian species against hemorrhagic enteritis comprising the supernatant fluid recovered from the in vitro propagation of hemorrhagic enteritis virus (HEV) on a culture of lymphoblastoid cells, wherein said cells have the characteristics of the MDTC-RP-19 cell line.

6. A vaccine as described in claim 5 wherein said virus is an avirulent strain of HEV.